(12) United States Patent
Pillai et al.

(10) Patent No.: US 8,568,435 B2
(45) Date of Patent: Oct. 29, 2013

(54) TRANSVASCULAR RETROGRADE ACCESS DEVICES

(71) Applicants: Lakshmikumar Pillai, Morgantown, WV (US); Paul A. LaDuca, Little Elm, TX (US); Frederich L. Alavar, San Jose, CA (US); Robert LaDuca, Santa Cruz, CA (US)

(72) Inventors: Lakshmikumar Pillai, Morgantown, WV (US); Paul A. LaDuca, Little Elm, TX (US); Frederich L. Alavar, San Jose, CA (US); Robert LaDuca, Santa Cruz, CA (US)

(73) Assignee: Vascular Access Technologies, Inc., Palo Alto, CA (US)

( * ) Notice: Subject to any disclaimer, the term of this patent is extended or adjusted under 35 U.S.C. 154(b) by 0 days.

(21) Appl. No.: 13/782,931

(22) Filed: Mar. 1, 2013

(65) Prior Publication Data

US 2013/0172922 A1 Jul. 4, 2013

Related U.S. Application Data

(62) Division of application No. 12/861,716, filed on Aug. 23, 2010, now Pat. No. 8,409,236.

(60) Provisional application No. 61/235,952, filed on Aug. 21, 2009.

(51) Int. Cl.
A61B 17/34 (2006.01)

(52) U.S. Cl.
USPC .......................................... 606/185; 606/170

(58) Field of Classification Search
USPC ......... 606/108, 159, 167, 170, 185, 192, 194, 606/195; 604/43, 164.01–164.12, 506–510, 604/532; 600/114–115, 424, 433
See application file for complete search history.

(56) References Cited

U.S. PATENT DOCUMENTS 4,559,039 A * 12/1985 Ash et al. ...................... 604/175
4,790,825 A * 12/1988 Bernstein et al. ......... 604/170.02
(Continued)

FOREIGN PATENT DOCUMENTS

WO WO 2004/018029 A2 3/2004
WO WO 2005/053547 A2 6/2005

OTHER PUBLICATIONS

Faul et al.; Vascular Disease Management; vol. 5; No. 5; pp. 128-133; Sep./Oct. 2008.

(Continued)

*Primary Examiner* — Ryan Severson
*Assistant Examiner* — David Eastwood
(74) *Attorney, Agent, or Firm* — Shay Glenn LLP

(57) ABSTRACT

A system for providing transvascular retrograde access in a central blood vessel of a patient. In some embodiments, the system has a handle; a catheter extending from the handle; and a tissue piercing element extending from the handle through the catheter, the tissue piercing element having a sharp distal tip adapted to extend from a distal portion of the catheter, the catheter and handle being adapted to be separated from the tissue piercing element, a distal portion of the tissue piercing element being adapted to serve as a guide for introduction of a device into the central blood vessel. The invention also includes a method of providing transvascular retrograde access to a central blood vessel of a patient.

10 Claims, 18 Drawing Sheets

(56) References Cited

U.S. PATENT DOCUMENTS

| | | | |
|---|---|---|---|
| 4,966,163 A | 10/1990 | Kraus et al. | |
| 5,421,348 A | 6/1995 | Larnard | |
| 5,492,530 A * | 2/1996 | Fischell et al. | 604/510 |
| 5,685,820 A | 11/1997 | Riek et al. | |
| 5,733,248 A | 3/1998 | Adams et al. | |
| 6,047,700 A | 4/2000 | Eggers et al. | |
| 6,102,926 A * | 8/2000 | Tartaglia et al. | 606/170 |
| 6,475,226 B1 | 11/2002 | Belef et al. | |
| 6,508,777 B1 | 1/2003 | Macoviak et al. | |
| 6,554,794 B1 * | 4/2003 | Mueller et al. | 604/95.04 |
| 6,655,386 B1 * | 12/2003 | Makower et al. | 128/898 |
| 6,726,677 B1 | 4/2004 | Flaherty et al. | |
| 7,008,979 B2 | 3/2006 | Schottman et al. | |
| 7,374,567 B2 | 5/2008 | Heuser | |
| 7,648,517 B2 | 1/2010 | Makower et al. | |
| 8,409,236 B2 | 4/2013 | Pillai | |
| 2001/0000041 A1 * | 3/2001 | Selmon et al. | 600/585 |
| 2001/0012924 A1 * | 8/2001 | Milo et al. | 604/164.08 |
| 2001/0023346 A1 * | 9/2001 | Loeb | 604/508 |
| 2002/0004666 A1 | 1/2002 | Schwager et al. | |
| 2002/0029060 A1 * | 3/2002 | Hogendijk | 606/185 |
| 2002/0120250 A1 * | 8/2002 | Altman | 604/508 |
| 2002/0133168 A1 * | 9/2002 | Smedley et al. | 606/108 |
| 2002/0169377 A1 * | 11/2002 | Khairkhahan et al. | 600/433 |
| 2004/0039371 A1 | 2/2004 | Tockman et al. | |
| 2004/0082850 A1 * | 4/2004 | Bonner et al. | 600/424 |
| 2004/0133168 A1 | 7/2004 | Salcudean et al. | |
| 2004/0181150 A1 * | 9/2004 | Evans et al. | 600/433 |
| 2004/0181238 A1 | 9/2004 | Zarbatany et al. | |
| 2005/0101984 A1 * | 5/2005 | Chanduszko et al. | 606/185 |
| 2005/0149097 A1 * | 7/2005 | Regnell et al. | 606/191 |
| 2006/0009715 A1 * | 1/2006 | Khairkhahan et al. | 600/585 |
| 2006/0009737 A1 * | 1/2006 | Whiting et al. | 604/135 |
| 2006/0135962 A1 * | 6/2006 | Kick et al. | 606/108 |
| 2006/0247750 A1 | 11/2006 | Seifert et al. | |
| 2007/0021767 A1 | 1/2007 | Breznock | |
| 2008/0082136 A1 | 4/2008 | Gaudini | |
| 2008/0215008 A1 * | 9/2008 | Nance et al. | 604/164.03 |
| 2008/0249565 A1 | 10/2008 | Michler et al. | |
| 2011/0178530 A1 | 7/2011 | Bly | |
| 2012/0136247 A1 | 5/2012 | Pillai | |
| 2012/0136366 A1 * | 5/2012 | Pillai | 606/108 |

OTHER PUBLICATIONS

Huang et al.; Evaluation of the needle technique for producing an arteriovenous fistula; Journal of Applied Physiology; vol. 77(6); pp. 2907-2911; Dec. 1994.

Khanna et al.; Sharpening of hollow silicon microneedles to reduce skin penetration force; J. Micromech. Microeng.; vol. 20; No. 4, pp. 045011 (8 pgs.); Mar. 15, 2010.

LuMEND, Inc.; Outback LTD re-entry catheter; Product Resources (http://www.lumend.com/Images/Technology/Product/brochure.pdf) This web address was available to applicant(s) at least as of (Jul. 19, 2006).

Mewissen, Mark; Revascularization of long FP arterial occlusions; Endovascular Today; pp. 2-4; Mar. 2004.

O'Callaghan et al.; Dynamics of stab wounds: force required for penetration of various cadaveric human tissues; Forensic Sci. Int'l; vol. 104; pp. 173-178; Oct. 11, 1999.

Pillai, Lakshmikumar; U.S. Appl. No. 11/381,229 entitled "Methods of Transvascular Retrograde Access Placement and Devices for Facilitating Therein," filed May 2, 2006.

* cited by examiner

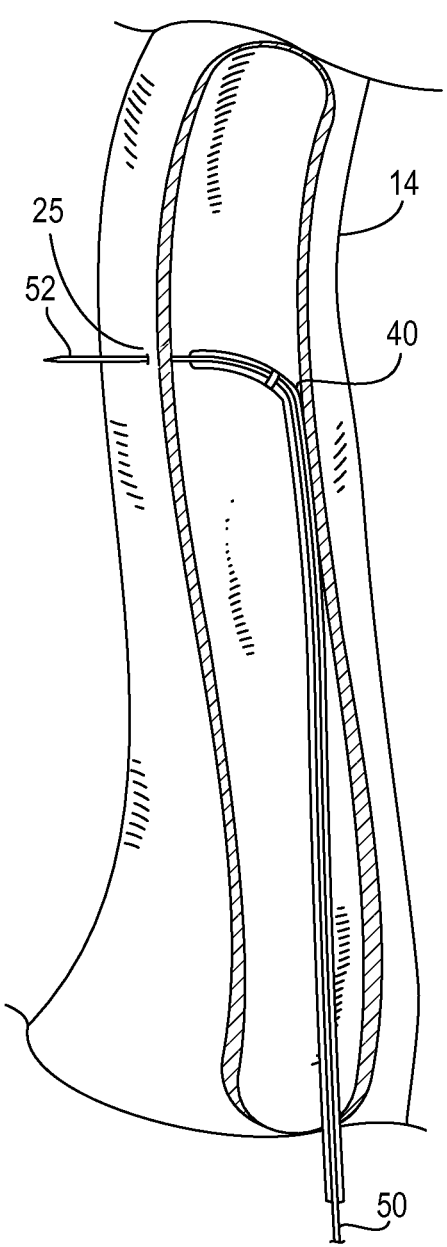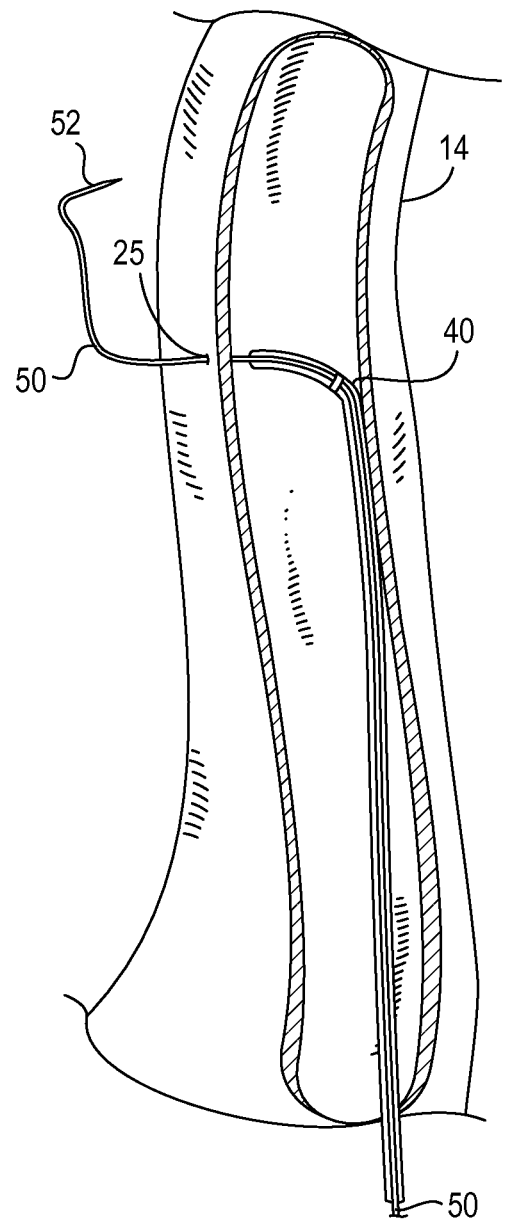
FIG. 7E
FIG. 7F

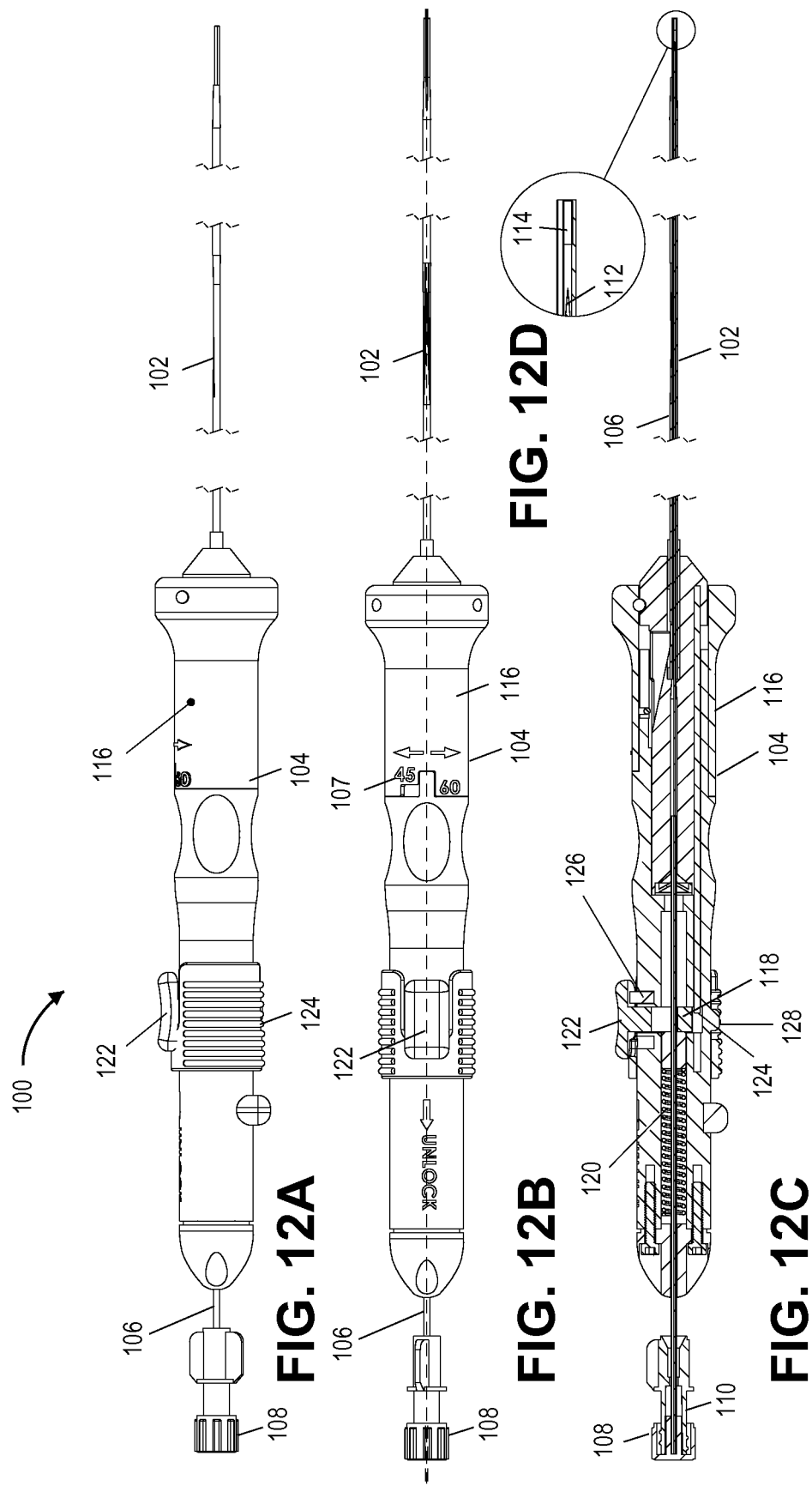

TRANSVASCULAR RETROGRADE ACCESS DEVICES

CROSS REFERENCE TO RELATED APPLICATIONS

This application is a divisional of U.S. application Ser. No. 12/861,716, filed Aug. 23, 2010, which application claims the benefit under 35 USC 119 to U.S. Provisional Application No. 61/235,952, filed Aug. 21, 2009, the disclosure of which is incorporated by reference as if fully set forth herein.

FIELD OF THE INVENTION

The present invention relates to methods and devices directed toward providing transvascular retrograde access placement in central vessels. More particularly, these methods and devices direct an initial passage of a needle tipped guidewire from the inside of the vessel to the outside, followed by guided insertion of a secondary catheter over the needle tipped guidewire into the vessel.

INCORPORATION BY REFERENCE

All publications, patents and patent applications mentioned in this specification, either by an inventor common to this application or by other inventors, are herein incorporated by reference to the same extent as if each individual publication, patent, or patent application was specifically and individually indicated to be incorporated by reference.

BACKGROUND OF THE INVENTION

Gaining direct access by way of a catheter to a central vein (one which goes directly to the heart) is a common procedure that is useful for a number of medical needs, including providing fluids and nutrition, administering drugs, and allowing access to the heart for cardiovascular measurements or the implantation of devices such as pacemakers. Conventional approaches for performing central venous catheterization, as shown in FIG. 1, generally involve the placing of catheters, needles and/or wires through a percutaneous entry site 1 into a jugular vein 14 or a subclavian vein 16 and subsequent central venous cannulation. This method involves inherent risks with potentially serious consequences and adverse effects to the patient due to the technique's essentially blind puncture through the skin and percutaneous tissue (i.e., from the outside of the skin to the inside of the central vein) overlaying an accessible site of the vein. More specifically, conventional techniques, with or without fluoroscopic guidance, involve percutaneous puncture of either the jugular or subclavian vein with a hollow needle, and the passage of a guidewire into the punctured vein through the needle. Thereafter, the guidewire assists with the insertion of a vascular catheter, which then ultimately replaces the guidewire. Theses central veins are deep structures, and cannot be visualized without imaging technology. The percutaneous puncture site generally is determined by anatomic landmarks ("dead reckoning") or, less commonly, with the aid of transcutaneous ultrasound.

While this conventional technique is usually accomplished with few or any complications and minimal pain to the patient, the technique, due to the essentially blind percutaneous puncture, inherently carries significant risks. These risks include potentially disabling or life-threatening injuries such as injury to adjacent vascular structures or nerves, occurrence of stroke secondary to vascular injury, or occurrence of pneumothorax or hemothorax secondary to lung injury. The risk of eventualities such as these are more likely when the technique is performed on children or on adult patients with challenging anatomy or conditions, such as emaciation or morbid obesity.

Safer and more cost-efficient alternative approaches to central vein access that obviate the need for blind percutaneous vein puncture would be a welcome addition to the possible approaches available to patients requiring central vein access. One such possible safer and more cost-efficient approach may include accessing the central blood vessel via a transvascular retrograde approach. The approach may be facilitated by devices and methods that provide accurate and controlled manipulation within the central blood vessel and while exiting the central blood vessel.

Reference is also made to U.S. application Ser. No. 12/366,517, entitled "Methods of Transvascular Retrograde Access Placement and Devices for Facilitating Therein", filed Feb. 5, 2009; which is a continuation-in-part of U.S. application Ser. No. 11/424,131, entitled "Methods of Transvascular Retrograde Access Placement and Devices for Facilitating Therein", filed Jun. 14, 2006; which is a continuation of U.S. application Ser. No. 11/381,229, filed May 2, 2006; all of which are incorporated by reference as if fully set forth herein.

SUMMARY OF THE INVENTION

Methods for performing transvascular retrograde access placement in a central blood vessel should be safe, accurate, and controlled. It is desirable that the methods, and the devices that facilitate them, include accurately positioning a portion of a vascular device, such as an angled catheter tip, into a desired position within a vessel. Once the portion of the device is positioned accurately within the vessel, it is desirable that a portion of the device or system, such as a needle tipped guidewire, may be moved through the device and/or through the vessel in a safe and controlled manner, such that it may exit the vessel in a safe and controlled manner.

Described herein are devices, systems and methods for performing transvascular retrograde access placement in a central blood vessel in a safe, accurate, and controlled manner. In general, the devices may include a catheter comprising an angled tip; a handle coupled to the catheter, the handle having a reference portion, wherein the position of the reference portion corresponds to the position of the angled tip; a locking mechanism, coupled to the handle, sized and configured to couple to a needle tipped guidewire; and a slider, coupled to the handle, sized and configured to advance the needle tipped guidewire through the catheter. In general, the methods may include positioning a catheter of a vascular device, the catheter comprising an angled tip, within the central blood vessel such that the angled tip faces a desired exit site on a wall of the central blood vessel and passing a needle tipped guidewire from the catheter through the desired exit site on the wall of the central blood vessel and skin of the patient.

One aspect of the invention provides a system for providing transvascular retrograde access in a central blood vessel of a patient. In some embodiments, the system includes a handle; a catheter extending from the handle; and a tissue piercing element extending from the handle through the catheter, the tissue piercing element comprising a sharp distal tip adapted to extend from a distal portion of the catheter, the catheter and handle being adapted to be separated from the tissue piercing element, a distal portion of the tissue piercing element being adapted to serve as a guide for introduction of a device into the central blood vessel. The distal end of the catheter may have an angled tip, and in some such embodiments the system may have a reference at a proximal end of the catheter indicating a bending direction of the angled tip.

In some embodiments, the handle comprises an actuator adapted to advance the tissue piercing element through an opening at the distal end of the catheter. The actuator may include a slider adapted to move within a slot in the handle. Alternatively or additionally, the actuator may include a spring and possibly a spring release element and/or an interlock having a first state adapted to prevent actuation of the actuator and a second state adapted to permit actuation of the actuator. The system may also have a lock having a first state adapted to prevent movement of the tissue piercing element with respect to the actuator and a second state adapted to permit movement of the tissue piercing element with respect to the actuator.

In some embodiments, the handle has a deflection actuator adapted to deflect a distal tip of the catheter away from a longitudinal axis of the catheter. In such embodiments the handle may also have a deflection indicator adapted to indicate an amount of deflection of the distal end of the catheter. Some embodiments of the system may also have an interlock adapted to prevent movement of the sharp tip of the tissue piercing element out of the distal portion of the catheter unless the distal portion of the catheter is deflected away from a longitudinal axis of the catheter.

Another aspect of the invention provides a method of providing transvascular retrograde access to a central blood vessel of a patient. Some embodiments of the method include the steps of inserting a distal end of a catheter into a blood vessel other than the central blood vessel, a proximal end of the catheter being connected to a handle disposed outside of the patient; advancing the distal end of the catheter into the central blood vessel; orienting the distal end of the catheter to an exit location within the central blood vessel; actuating a tissue piercer actuator of the handle to advance a tissue piercing element from the catheter through the central blood vessel at the exit location; and introducing a device over the tissue piercing element through the exit location into the central blood vessel.

In some embodiments, the orienting step includes the step of rotating the catheter with respect to the patient, such as by rotating the handle and catheter together. In some embodiments, the orienting step includes the step of bending the distal end of the catheter with respect to a longitudinal axis of the catheter, such as by moving a bending actuator of the handle. In such embodiments, the method may also include the step of preventing actuation of the tissue piercer actuator if catheter distal end is not bent.

In some embodiments, the step of actuating the tissue piercer includes the step of sliding the tissue piercer actuator within a slot in the handle. In some embodiments, the step of actuating the tissue piercer includes the step of releasing a spring within the handle, such as by actuating a spring release element to release the spring.

Some embodiments of the method include the step of actuating a spring release element to release the spring. In some embodiments, the method includes the step of locking the tissue piercing element to the tissue piercer actuator prior to actuating the tissue piercing actuator.

The invention will be explained in more detail below with reference to the drawings.

BRIEF DESCRIPTION OF THE FIGURES

FIGS. 7A-7F show an embodiment of a method that makes use catheter with an angled tip, with a focus on the activity that occurs at the site of exit from the jugular vein and re-entry there into. FIG. 7A shows the approach of a general use guidewire to the vicinity of a desired exit site in a jugular vein.

FIG. 7B shows the approach of a vascular catheter over a general use guidewire to the vicinity of the desired exit site in the jugular vein.

FIG. 7C shows the angled-tip vascular catheter with the general use guidewire having been withdrawn and a stiff guidewire with a penetrating device on its distal end being advanced to the distal end the curved tip vascular catheter.

FIG. 7D shows the angled vascular tip catheter rotating toward a desired exit site on the wall of the jugular vein, the site of exit on an exterior facing aspect of the vein, the rotation being driven by torque applied at the proximal end of the catheter.

FIG. 7E shows the penetrating device mounted on the distal end of the stiff guidewire advancing out of the vascular catheter, and penetrating outwardly through the wall of the jugular vein into neck muscle and subcutaneous tissue.

FIG. 7F shows the penetrating device penetrating further outward through the skin of the neck and from the body, the stiff intravascular guidewire trailing behind. (Hereinafter, the method proceeds as depicted in FIGS. 6A-6D.)

FIGS. 12A-D show yet another embodiment of a system for providing transvascular retrograde access in a central blood vessel of a patient.

DETAILED DESCRIPTION OF THE INVENTION

Described herein are devices, systems and methods for performing transvascular retrograde access placement in a central blood vessel in a safe, accurate, and controlled manner. In general, the devices may include a catheter comprising an angled tip; a handle coupled to the catheter, the handle having a reference portion, wherein the position of the reference portion corresponds to the position of the angled tip; a locking mechanism, coupled to the handle, sized and configured to couple to a needle tipped guidewire; and a slider, coupled to the handle, sized and configured to advance the needle tipped guidewire through the catheter. In general, the methods may include positioning a catheter of a vascular device, the catheter comprising an angled tip, within the central blood vessel such that the angled tip faces a desired exit site on a wall of the central blood vessel and passing a needle tipped guidewire from the catheter through the desired exit site on the wall of the central blood vessel and skin of the patient.

Figure 1:
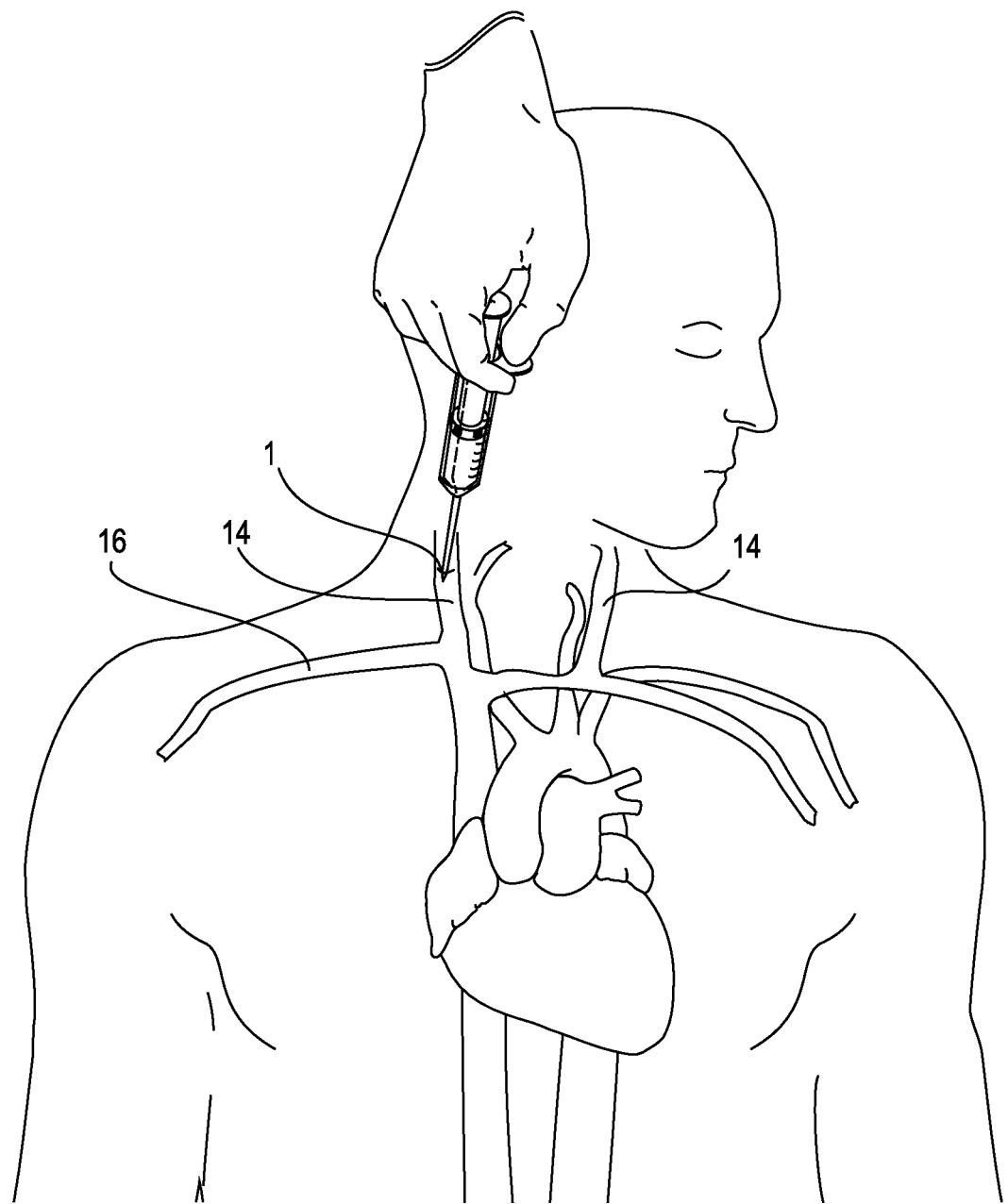
FIG. 1 shows a conventional technique of the prior art of performing upper trunk central venous catheterization.

Embodiments of a method of the transvascular retrograde access placement, as provided herein, include the puncturing of a central blood vessel from the inside of the vessel with a penetrating device, such as a needle tipped guidewire or other similarly configured device, and exiting that penetrating device from a patient through the skin. By such an inside-to-outside approach, the ability of a surgeon to precisely determine the location of a pass-through site in the vascular wall is substantially enhanced over prior art methods that rely on a conventional outside-to-inside approach, as shown in FIG. 1. After the penetrating device penetrates through the skin to the exterior of the body, a vascular catheter may be inserted into the central blood vessel by passing the catheter over the penetrating device in a retrograde direction.

The devices, systems, methods, and any combination thereof for performing transvascular retrograde access placement in a central blood vessel described herein provide at least the following advantages. First, they may be safer and pose less risk to the patient. Furthermore, as described herein, the methods, and the devices that facilitate them, include accurately positioning a portion of a vascular device, such as an angled catheter tip, into a desired position within a vessel. Once the portion of the device is positioned accurately within the vessel, a second portion of the device or system, such as a needle tipped guidewire, may be moved through the device and/or through the vessel in a safe and controlled manner, such that it may exit the vessel in a safe and controlled manner.

Embodiments of the method and devices for implementing the method are directed toward various regions of the vascular system, in accordance with particular medical indications. One particular use of the methods of the invention is for central vein access, in which a central vein, such as a jugular vein or subclavian vein is accessed. The initial approach to the central vein, by way of a guidewire, followed by a vascular catheter, is by way entry into a primary vein, such as femoral vein or antecubital vein. Thereafter, a penetrating element, positioned by advancement from the primary vein site of entry to a desired site of exit in the central vein, creates an opening through the vessel wall and overlaying skin. That site of exit, in turn, becomes the site of re-entry for a central vein catheter. Inasmuch as what is initially formed as an exit site from the vessel can later be used as a site for entry for a central vein catheter, the site of opening/entry may also be neutrally referred to as a vascular pass-through site.

Embodiments of the invention, while generally described and depicted herein in the context of providing retrograde access into a central vein through an opening originally formed as an exit from the central vein, the invention may also be generally understood as providing methods of vascular entry through an exit-formed opening in blood vessels other than a central vein. This method embodiment includes positioning a vascular catheter within a blood vessel such that a portion of the vascular catheter faces a desired exit site on a wall of the blood vessel, passing a penetrating device that is advanced from the vascular catheter through the desired exit site on the wall of the blood vessel and a skin site of the patient overlaying the desired exit site, and passing an end of a secondary vascular catheter through the exit site and into the blood vessel. In various embodiments of this method, the blood vessel may be a vein, a central vein, or an artery. An example of an artery that is particularly difficult to access externally is the subclavian artery, thus there may be advantages to accessing the subclavian artery by such methods as described herein.

The primary blood vessel cannulation may be achieved by means of the Modified Seldinger Technique, wherein the desired vessel or cavity is punctured with a sharp hollow needle; a round-tipped guidewire is then advanced through the lumen of the needle, and the needle is withdrawn. An introducer is then inserted over the round-tipped guidewire, and into the vessel; a "sheath" or blunt cannula is passed through the introducer; and the guidewire and introducer are then withdrawn. The sheath can then be used to introduce catheters into the vessel.

Figure 2:
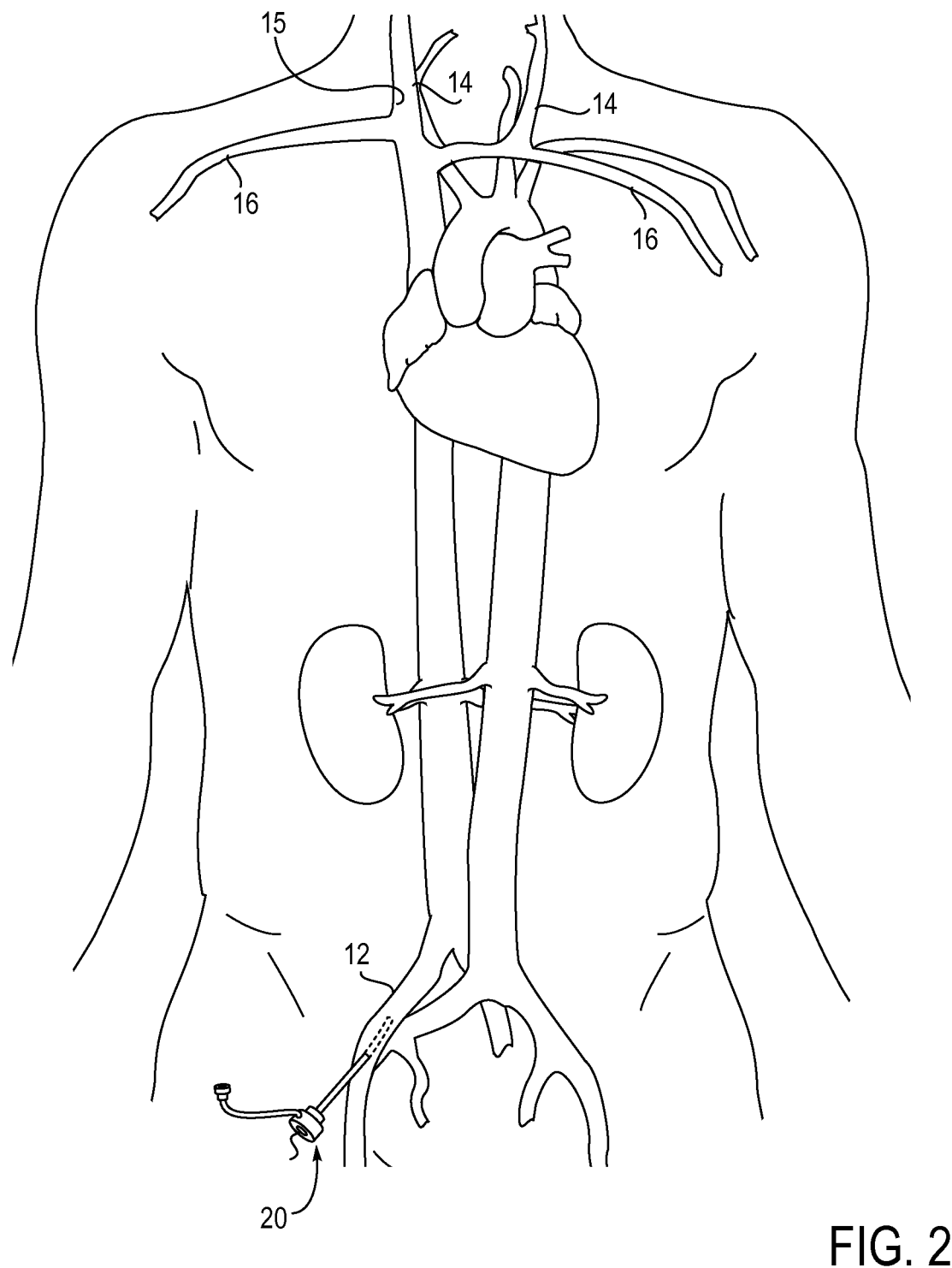
FIG. 2 shows a vascular sheath inserted into a femoral vein of the central venous system of a patient.

In accordance with the methods of the present invention, the Modified Seldinger Technique typically is performed with an 18-gauge hollow needle about 2⅞ inches in length, and a 5 cc syringe secured to the end of the 18-gauge needle opposite of the needle-tip. As shown in FIG. 2, a femoral vein 12 may be percutaneously cannulated with the needle. Once blood from the femoral vein 12 is aspirated into the syringe, the syringe is removed while the needle is held in place. Through this needle, a short guidewire, such as a J-tip wire measuring about 0.035 inches in diameter and about 20 centimeters in length may be advanced up the femoral vein 12 and into the iliac vein. The needle is then removed while the short guidewire is held in place. Thereafter, as shown in FIG. 2, a vascular sheath 20, generally measuring about 10 centimeters in length and typically but not necessarily including a removable stiff introducer and a hemostatic valve, is advanced over the short guidewire and into the femoral vein 12. The vascular sheath 20 is typically a 5 French (F) sheath, but may be a 6F or a 4F sheath, or another similarly sized and configured sheath. (French/3.14=inner diameter of a sheath or catheter in millimeters).

Then, with the vascular sheath 20 being substantially introduced into the patient, the short guidewire and the stiff introducer are removed and the vascular sheath 20 may be flushed by inserting heparinized saline solution into the vascular sheath 20 through the hemostatic valve. In various embodiments of the methods of the present invention, the Modified Seldinger Technique may be performed with other similarly sized and configured needles, syringes, sheaths, and/or wires.

Figure 3:
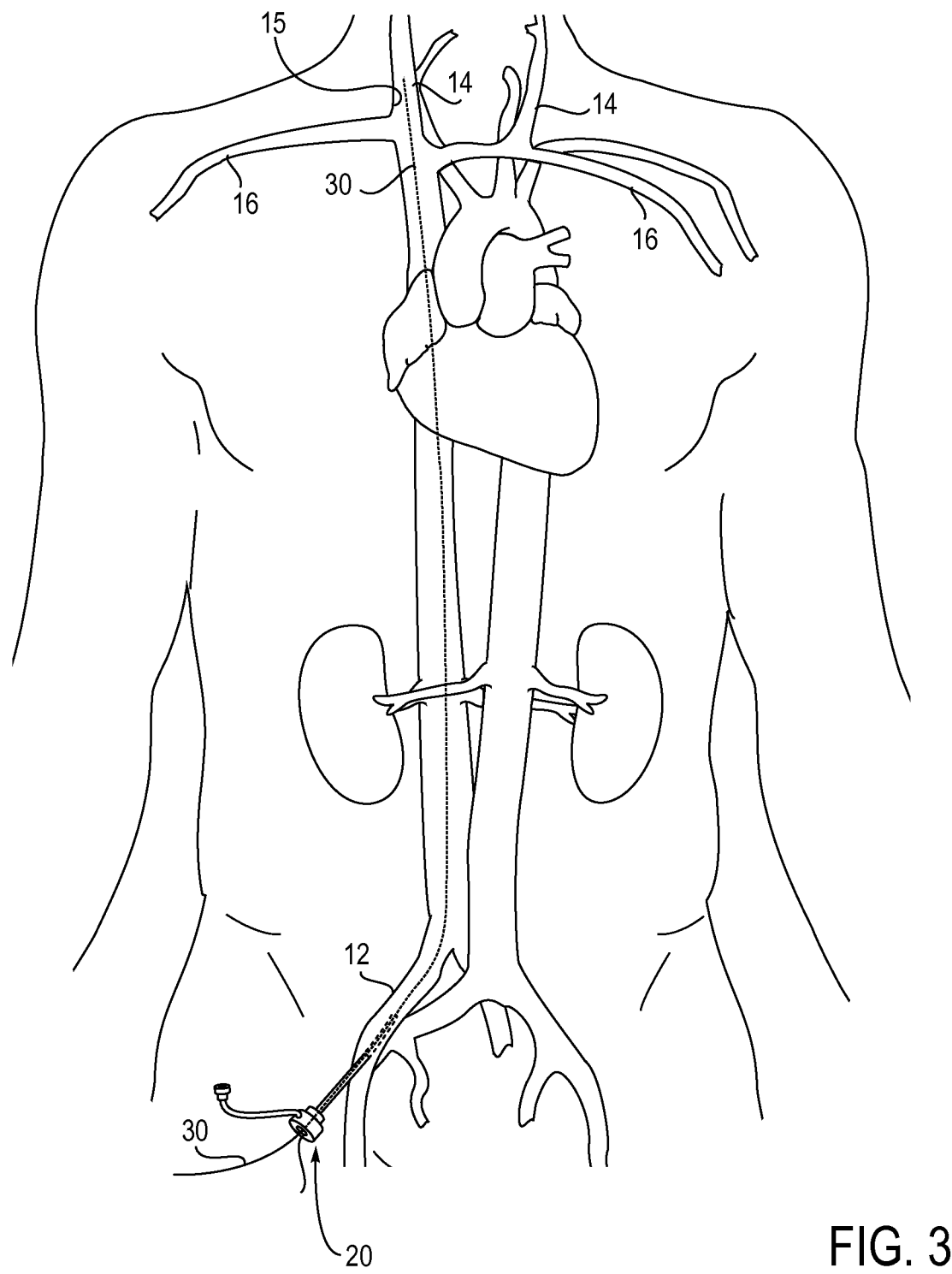
FIG. 3 shows a general use guidewire passed through a femoral venous vascular sheath and the venae cavae to a jugular vein.

Thereafter in furtherance of embodiments of the method, as shown in FIG. 3, a general use guidewire 30 typically measuring about 0.035 inches in diameter may be passed through the vascular sheath 20 and ultimately positioned in a jugular vein 14 in the vicinity of a desired exit and reentry site (or pass-through site) for central vein access. Following the insertion and positioning of the general use guidewire 30, an inventive angled-tip vascular catheter 40 may be passed over the general use guidewire 30, as shown in FIG. 4, after which the general use guidewire 30 is removed.

Figure 4:
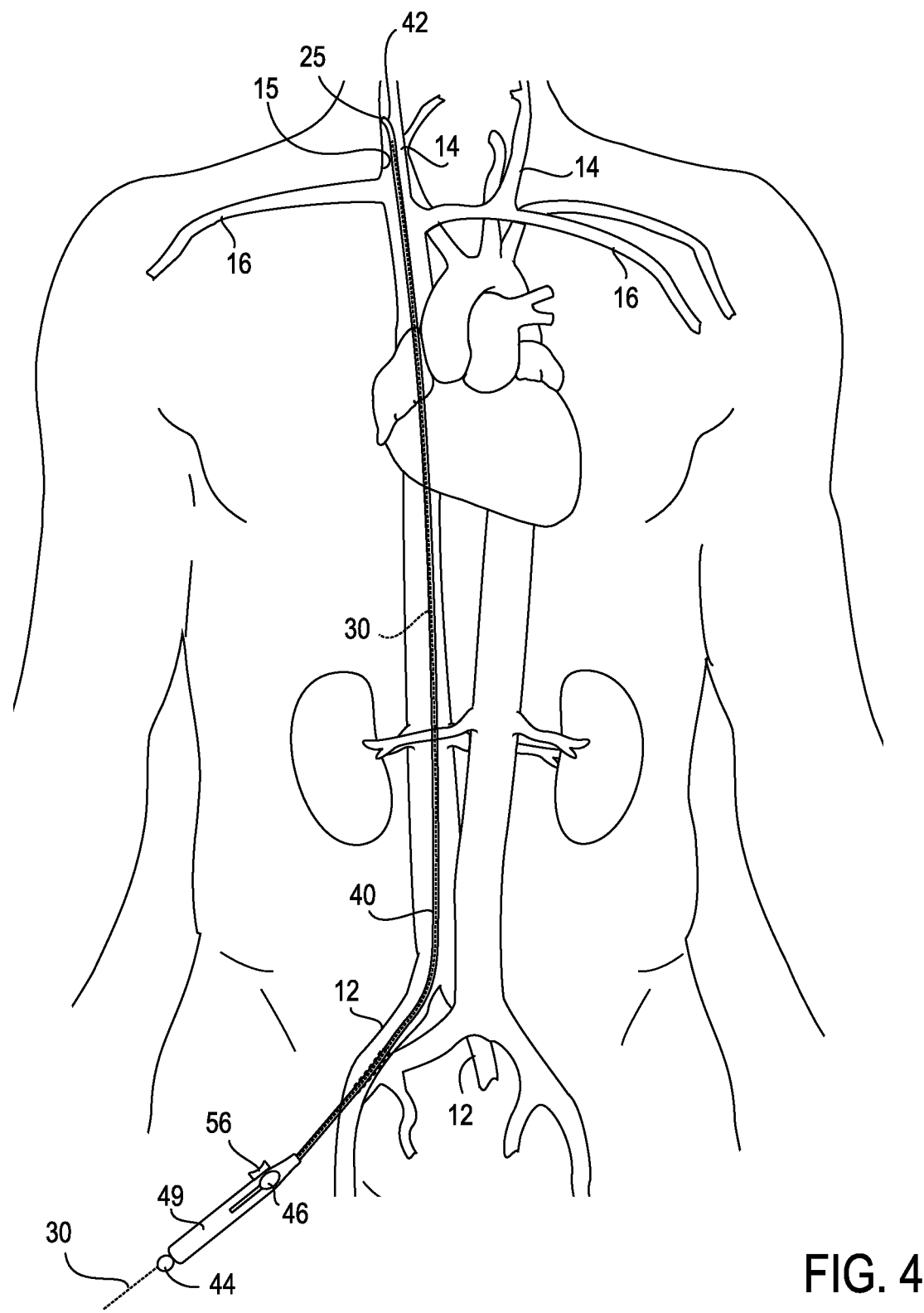
FIG. 4 shows an angled-tip vascular catheter passed over a general use guidewire and to a jugular vein.
Figure 5:
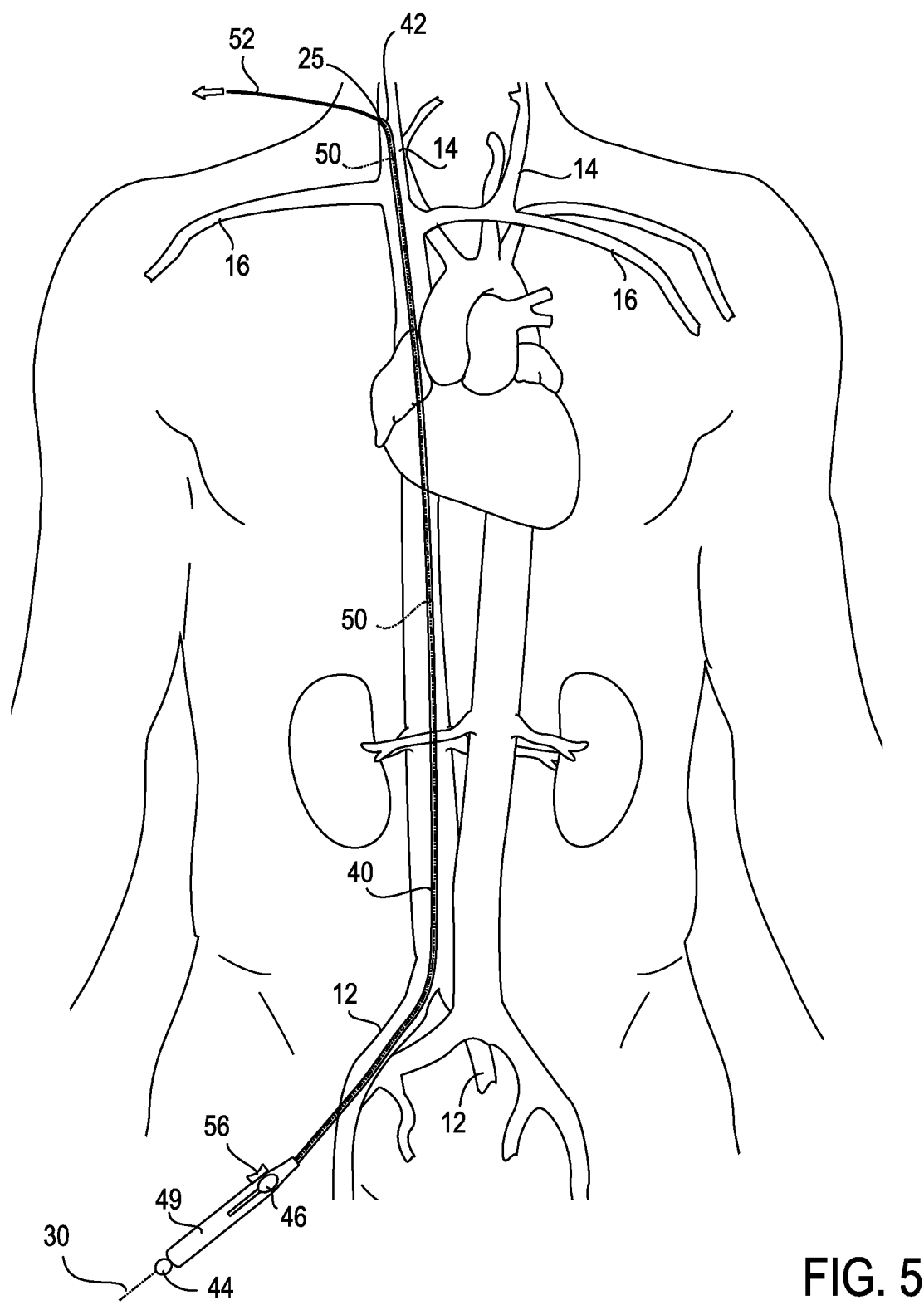
FIG. 5 shows an embodiment of a needle-tipped guidewire of the present invention inserted, via the femoral venous vascular sheath, through the angled-tip vascular catheter and used to puncture the wall of the jugular vein.

Continuing with embodiments of the method, as shown in FIG. 4, the vascular catheter 40 may then be positioned in the jugular vein 14 with the angled-tip 42 facing the interior wall 15 of the jugular vein 14 at a desired exit site 25. As depicted in FIG. 5, once the vascular catheter 40 is properly positioned, under continuing diagnostic imaging, as in some embodiments, a needle or other similarly configured sharp-tipped device or otherwise penetrating device, such as a needle-tip portion 52 of a stiff intravascular tissue-penetrating guidewire 50, may be passed through the end of the angled-tip 42 of the vascular catheter 40 and further pass through or penetrate the wall 15 of the jugular vein 14. Thereafter, the vascular wall penetrating device such as the needle, or the needle-tip portion 52 and a length of the needle-tipped guidewire 50 are passed through the subcutaneous tissue and exited through the skin of the patient (typically at mid-neck area when the central blood vessel punctured is a jugular vein 14) where they are recovered and pulled above the surface of the skin, as shown in FIG. 5. The vascular catheter 40 may then be removed from the vascular system of the patient, leaving the needle-tipped guidewire 50 in position.

Figure 6A:
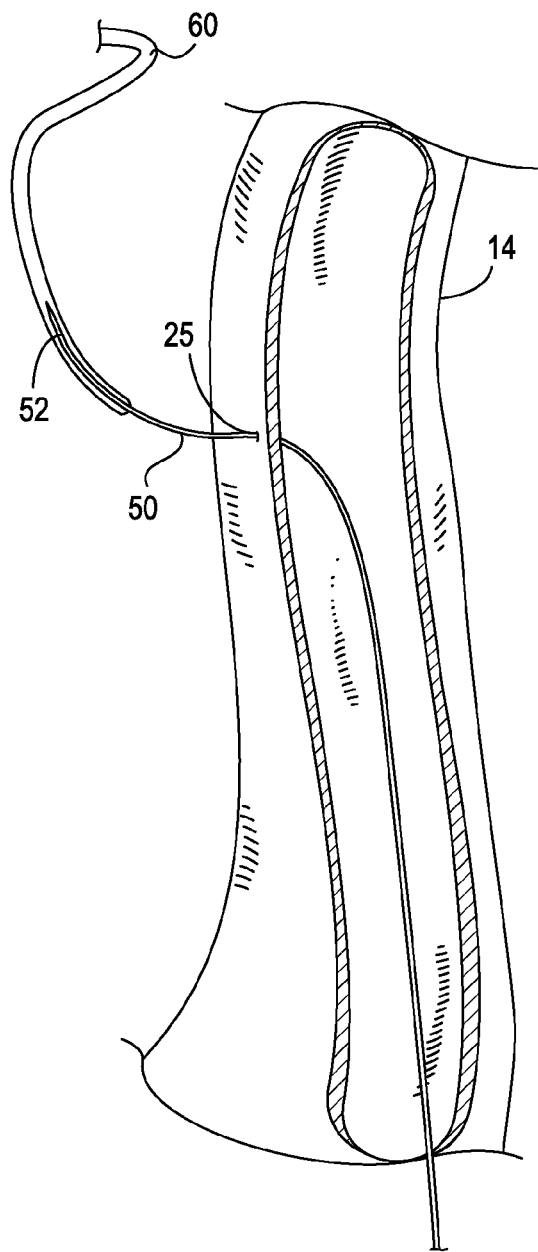
FIG. 6A shows a secondary vascular catheter being passed over the stiff intravascular guidewire, now outside the body, in a retrograde direction, from the distal end of the guidewire toward the proximal end. In some embodiments of the method, the penetrating device is removed from the distal end of the guidewire at this point.

FIG. 6A shows a secondary vascular catheter 60 being passed over the stiff intravascular guidewire 50, now outside the body, in a retrograde direction, from the distal end of the guidewire toward the proximal end. In some embodiments of the method, the penetrating device 52 is removed from the distal end of the guidewire 50 at this point.

Figure 6B:
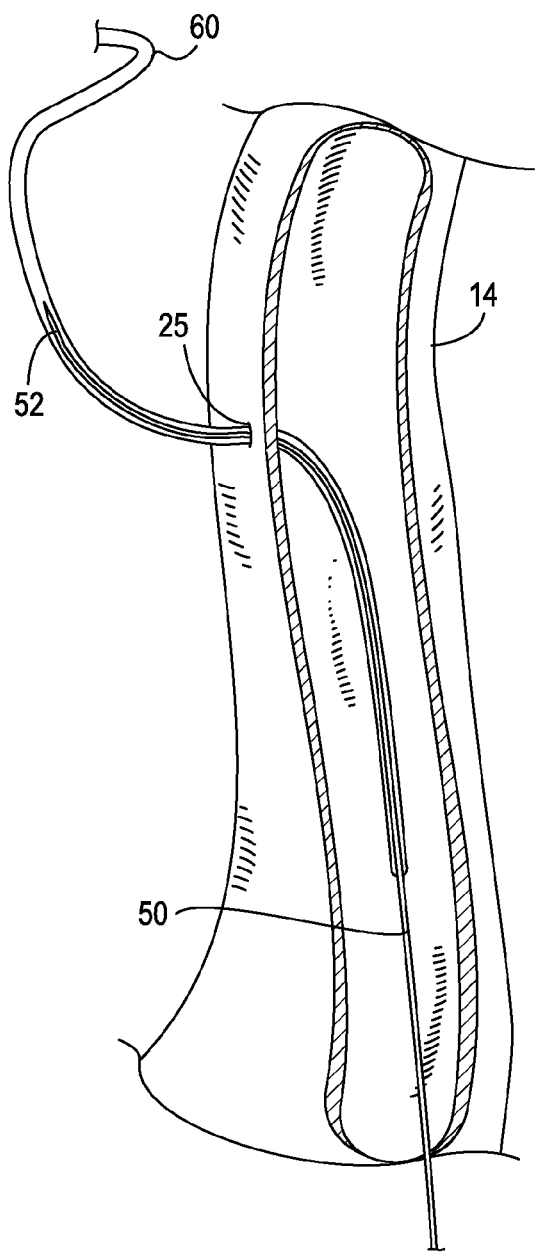
FIG. 6B shows the secondary vascular catheter entering the jugular vein in a retrograde direction, in the direction of venous blood flow, over the stiff intravascular guidewire.
Figures 6C, 6D:
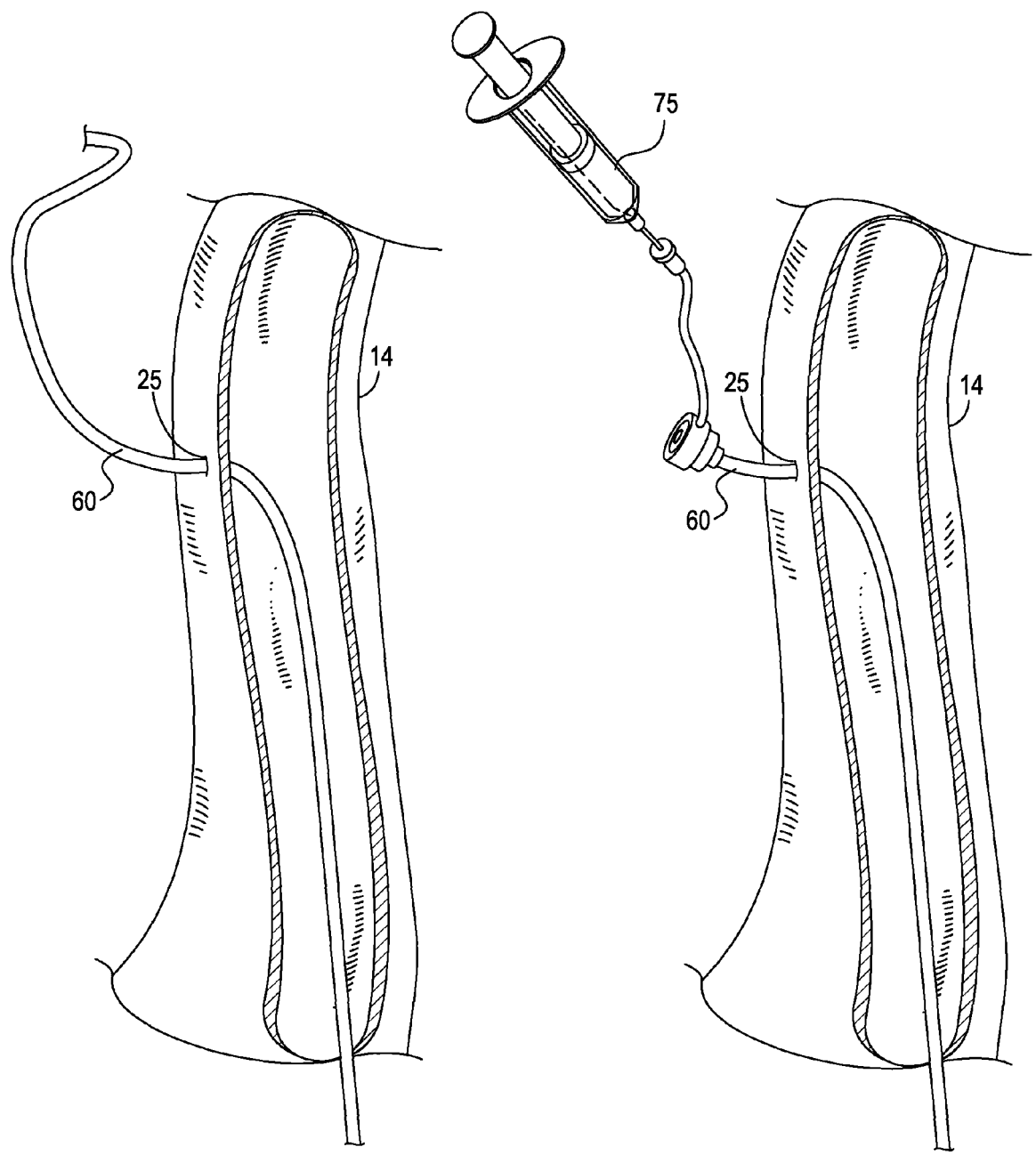
FIG. 6C shows the secondary vascular catheter in place in the jugular vein and positioned to act as a vascular access port, the stiff intravascular guidewire having been withdrawn from the jugular vein, ultimately to exit through its femoral vein site of entry.
FIG. 6D shows the secondary vascular catheter in place in the jugular vein as a vascular access port, and as an example of use, a syringe centrally administering drug through the central vein access port.

FIG. 6B shows the secondary vascular catheter 60 entering the jugular vein 14 in a retrograde direction (in the direction of venous blood flow) over the stiff intravascular guidewire 50. FIG. 6C shows the secondary vascular catheter 60 in place in the jugular vein 14 and positioned to act as a vascular access port, the stiff intravascular guidewire having been withdrawn from the jugular vein, ultimately to exit through its femoral vein site of entry. FIG. 6D shows the secondary vascular catheter 60 in place in the jugular vein 14 as a vascular access port, and as an example of use, a syringe 75 centrally administering drug through the central vein access port.

Figure 7A:
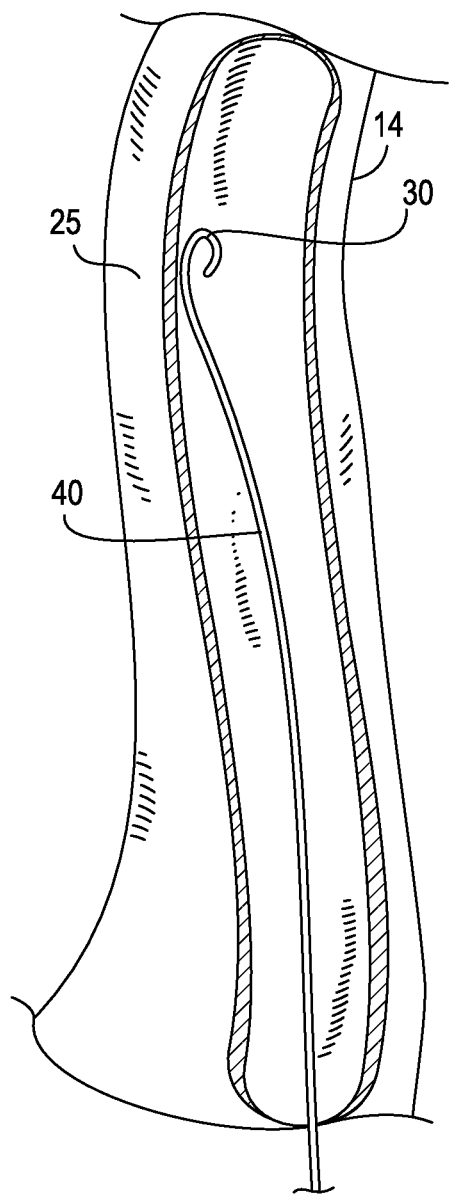
Figure 7B:
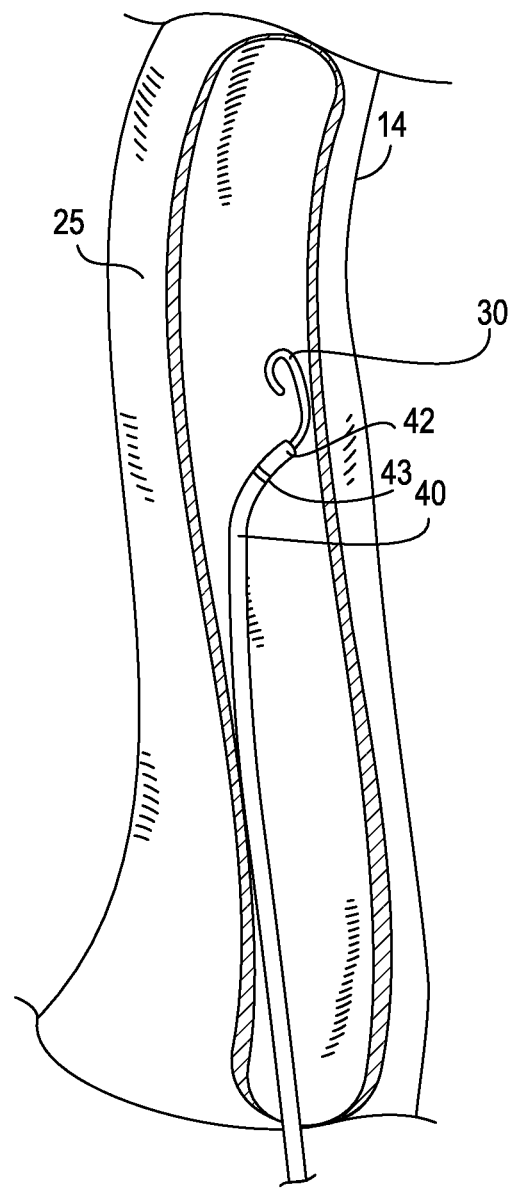

FIGS. 7A-7F focus on the activity that occurs at the site of exit from the jugular vein and re-entry there into. FIG. 7A shows the approach of a general use guidewire 30 to the vicinity of a desired exit site in the jugular vein. FIG. 7B shows the approach of a vascular catheter 40 over the general use guidewire 30 to the vicinity of the desired exit site 25 in the jugular vein 14. The curved or angled tip 42 of the vascular catheter has an angle of about 45 degrees from the central longitudinal axis of the catheter, and may be diagnostically visualizable by the radiopaque marking 43.

Figure 7C:
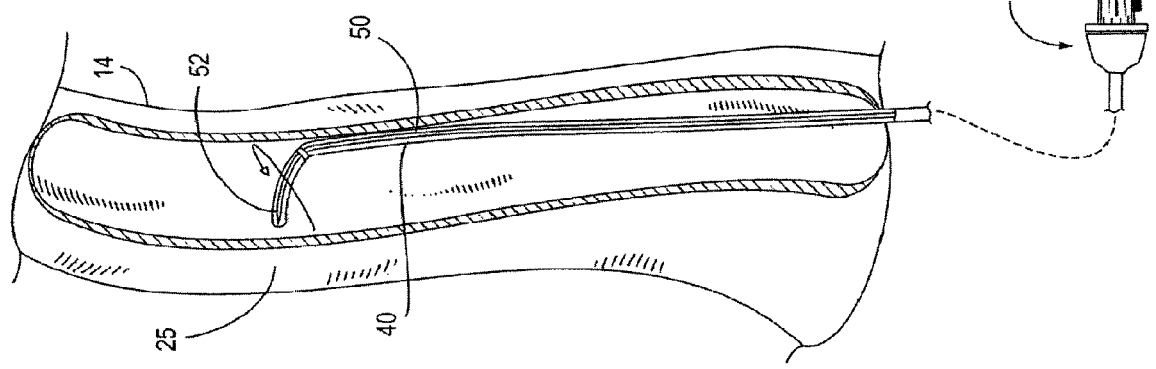
Figure 7D:
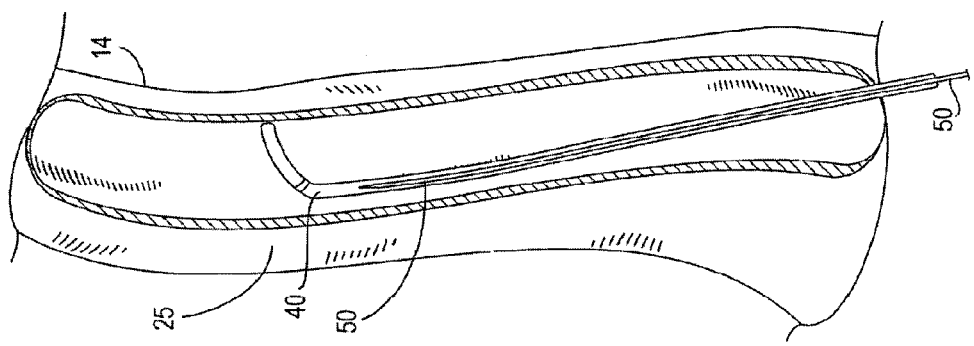

FIG. 7C shows the angled-tip vascular catheter 40 with the general use guidewire having been withdrawn from the catheter, and a stiff guidewire 50 with a penetrating device 52 (such as a needle tip) on its distal end having been advanced to the distal end of the angled tip vascular catheter. FIG. 7D shows the angled vascular tip catheter 40 rotating toward a desired exit site on the wall of the jugular vein. The site of vascular exit 25 is on a body exterior-facing aspect of the vein, so the penetrating device that eventually is expressed through the catheter is directed toward the skin, and not internally into the neck. The rotation is being driven by torque applied by a physician to a torqueable handle 49 on the catheter at its proximal end.

FIG. 7E shows the penetrating device 52 mounted on the distal end of the stiff guidewire 50 advancing out of the distal opening of the vascular catheter and directly into the wall at the exit site 25, penetrating outwardly through the wall of the jugular vein into neck muscle and subcutaneous tissue. FIG. 7F shows the penetrating device penetrating further outward through the skin of the neck and from the body, the stiff intravascular guidewire trailing behind. Hereinafter, the method proceeds as depicted in FIGS. 6A-6D, wherein, briefly, as the penetrating device and attached guidewire are outside the body, a secondary vascular catheter is passed in a retrograde direction over the guidewire, through the exit site, and into the jugular vein. In an optional step, the penetrating device may be removed from the guidewire prior to the secondary vascular catheter being passed there over. After insertion of the vascular catheter, the guidewire is removed from the jugular vein, typically through its site of entry in the femoral vein, and the secondary vascular catheter remains in place as a central vein access port.

Other embodiments of the methods of transvascular retrograde access placement procedure may be performed in a central blood vessel other than the jugular vein, wherein the needle, the needle-tipped guidewire, or any other similar device, may exit the patient through another area of the patient. For example, the transvascular retrograde access placement procedure may be performed in a subclavian vein, wherein a needle, a needle-tipped guidewire, or other similar device exits the patient through skin of the upper trunk just below a clavicle. In still other embodiments of the method, a blood vessel other than a central vein, such as a peripheral vein or an artery, may be accessed by re-entry into an opening created by outward penetration from within the vessel. The method may be particularly advantageous when external access to the vessel is complicated by normal anatomy (such being the case with the subclavian artery, for example), or by a complicating injury or medical condition.

Figure 8:
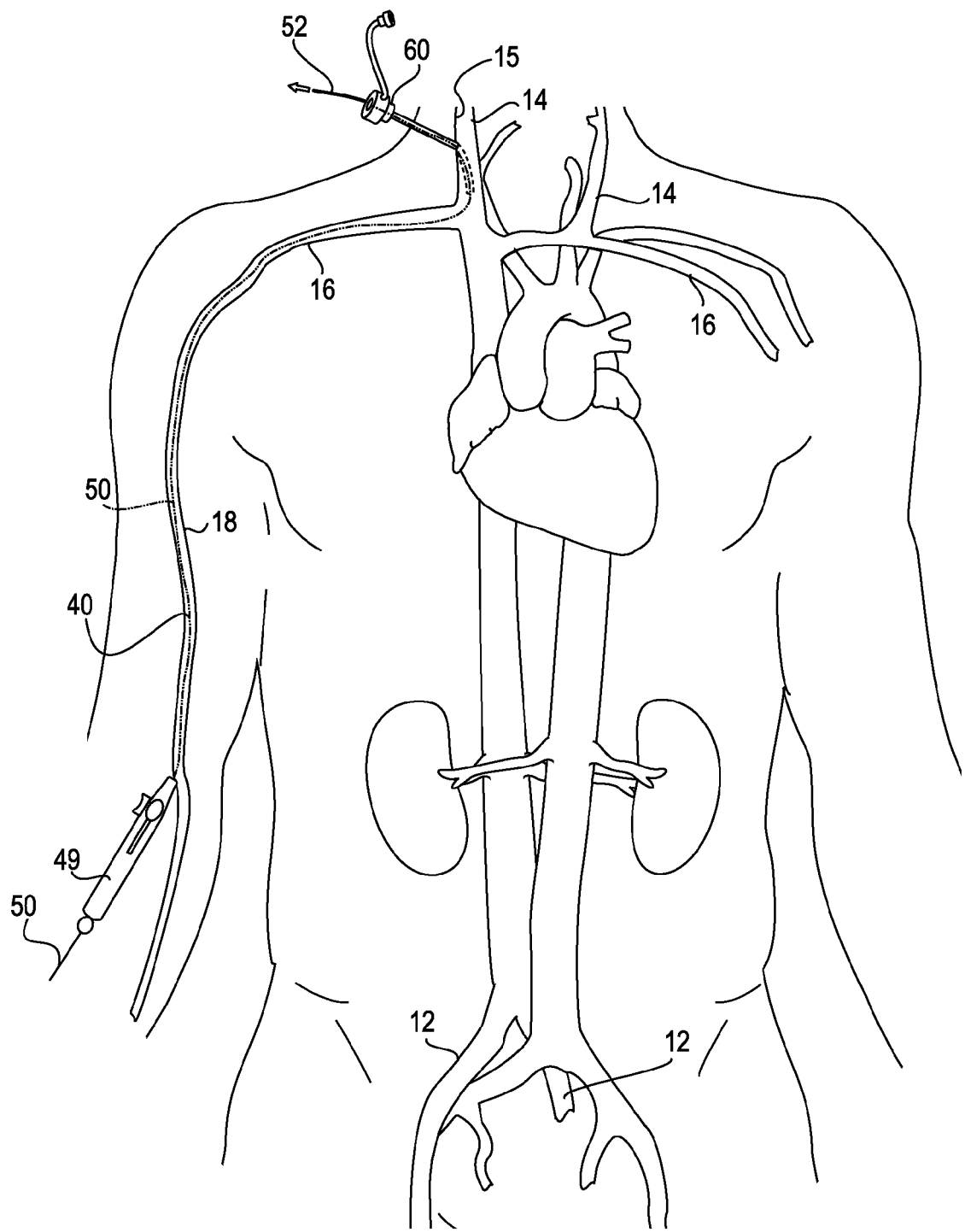
FIG. 8 shows an embodiment of the method wherein an angled catheter enters the vascular system through an antecubital vein and is advanced to a desired exit site in the jugular vein, where a tissue-penetrating device is delivered through the catheter to form a pass-though into which a retrograde jugular vein access device may be placed.

Another embodiment of the method of transvascular retrograde access placement varies from the previously described methods in that rather than approaching the central vein by way of femoral vein cannulation, an antecubital blood vein or artery (located in the antecubital fossa of an arm) is cannulated. As shown in FIG. 8, this method embodiment more specifically includes, through the application of the Modified Seldinger Technique and the insertion of a vascular sheath, inserting a general use guidewire into an antecubital vein 18 and then passing a vascular catheter 40, per embodiments of the invention, over the guidewire. The vascular catheter 40 is then passed up the vascular system to a jugular vein 14, or a subclavian 16 vein, or any other central vein. The procedure thus generally follows the steps depicted in FIGS. 2-5, except for the entry through the antecubital vein rather than the femoral vein. After the moment depicted in FIG. 8, the remainder of this method embodiment typically proceeds in accordance with the previously described embodiments of the present invention, as shown, for example, in FIGS. 6A-6D.

Figure 9A:
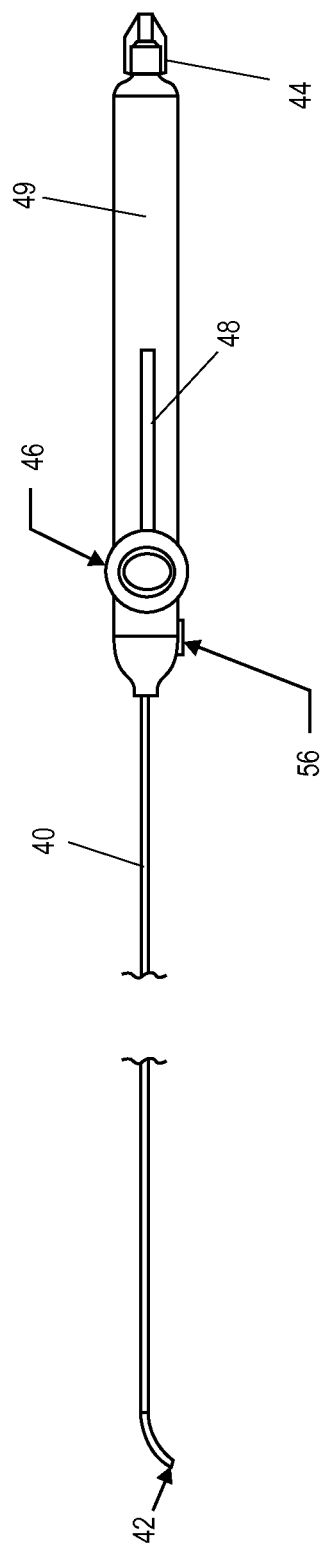
FIG. 9A shows an embodiment of a vascular device having an angled tip catheter and a handle having a slider, a reference portion, and a locking mechanism.

As has been noted in the description focused on embodiments of the method of transvascular retrograde access placement, the present invention also provides systems, devices and device features, some of which will now be described in greater detail. One such device, as shown in FIG. 9A, for performing transvascular retrograde access placement in a vessel of a patient may include a catheter 40 having an angled tip 42, a handle 49 coupled to the catheter, and a slider 46 coupled to the handle. The handle has a reference portion 56. As shown, the position of the reference portion with respect to the handle indicates the position of the angled tip 42 with respect to the handle. The handle also includes a locking mechanism that is sized and configured to couple to a needle tipped guidewire (not shown), such as the guidewire 50 shown in FIG. 5. The slider 46 is sized and configured to advance the needle tipped guidewire through the catheter 40. The device may be designed as a one-time-use disposable device. Alternatively, the device may be configured to be re-sterilized. The device may be distributed in a sterile barrier, such as Tyvek® or similar.

As shown in FIGS. 5 and 9A, the catheter 40 has an angled tip 42, and is sized and configured to guide a needle tipped guidewire 50 to the desired exit site on the wall of the central blood vessel (such as jugular vein 14). Embodiments of the inventive angled-tip vascular catheter 40 are typically a 5F catheter, but may be a 4F catheter, or another similarly sized and configured catheter. Embodiments of a vascular catheter 40 generally measure about 90 to 100 centimeters in length and include or support an angled-tip 42 that is typically angled at about 45 degrees from the axis of the vascular catheter 40 and is about 1.5 centimeters in length. Alternatively, as shown in FIG. 9A, the angled-tip 42 that is typically angled at about 55 to 75 degrees from the axis of the vascular catheter 40. Vascular catheter 40 may further include a lubricious coating on its inner and/or outer surfaces. The catheter has a lumen disposed along the length of the catheter. The inner diameter of the catheter may be 0.02" to 0.08". For example, the inner diameter of the catheter may be 0.047", or any other suitable dimension. The catheter may be sized and configured to be placed over and/or advanced over a general use guidewire 30, as shown in FIG. 5. Additionally or alternatively, the catheter may be sized and configured to be compatible with a general use femoral introducer sheath. Furthermore, the catheter may be designed to be used in a standard catheter lab under fluoroscopy or other visualization mechanism.

As shown in FIGS. 4, 5, and 9A, the handle 49 is coupled to the catheter 40 and facilitates the insertion of the catheter 40 and the needle tipped guidewire 50. The handle has a lumen disposed along the length of the handle that is along the axis of the lumen of the catheter 40. The inner diameter of the handle may be 0.01" to 0.07". For example, the inner diameter of the handle may be 0.038", or any other suitable dimension. The lumen of the handle may be smaller than the lumen of the catheter 40 to facilitate the insertion and the guidance of a needle tipped guidewire into the handle and catheter. The handle is sized and configured to be held in a hand or hands of a user and manipulated to move the catheter 40 and/or a needle tipped guidewire within the catheter within a vessel of a patient. For example, the handle may be 5 to 8" long, such as 7.75" long, or any other suitable length.

Figure 9B:
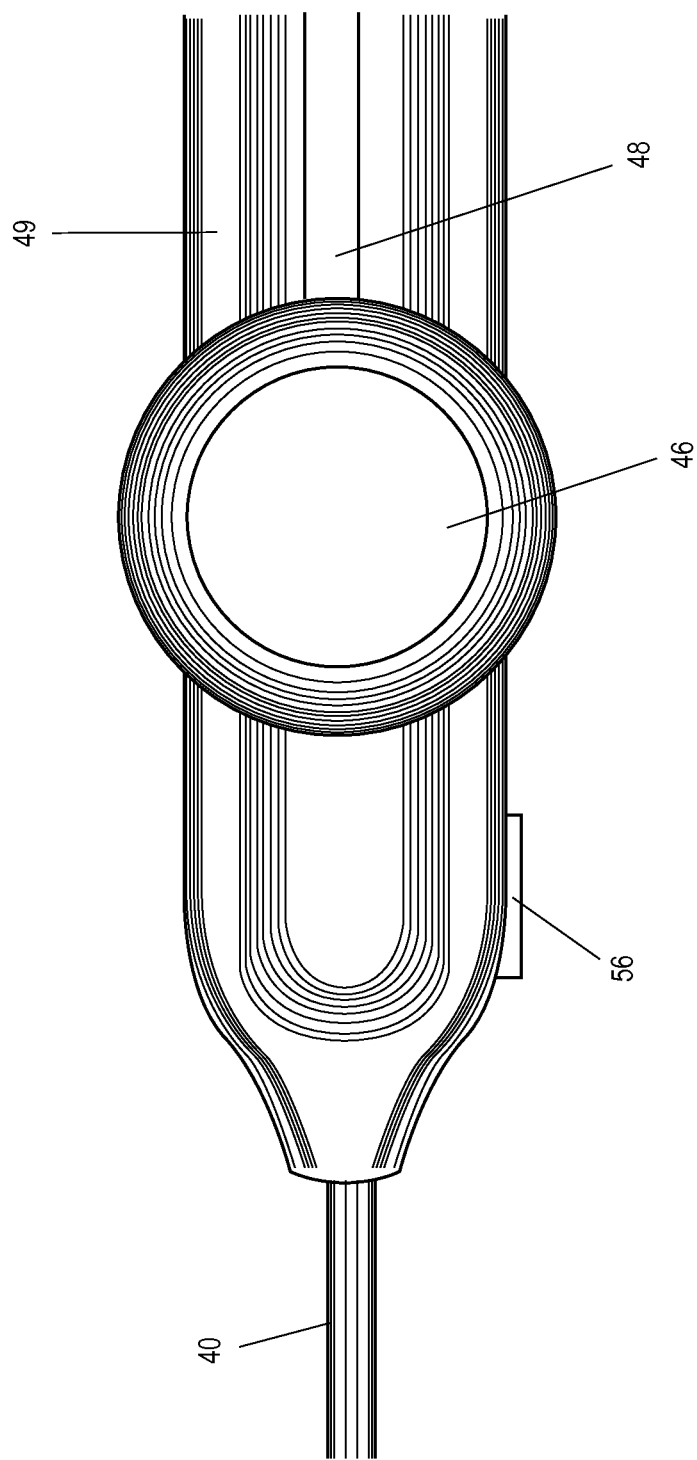
FIG. 9B shows a larger view of the handle of FIG. 9A having a slider and a reference portion.
Figure 9C:
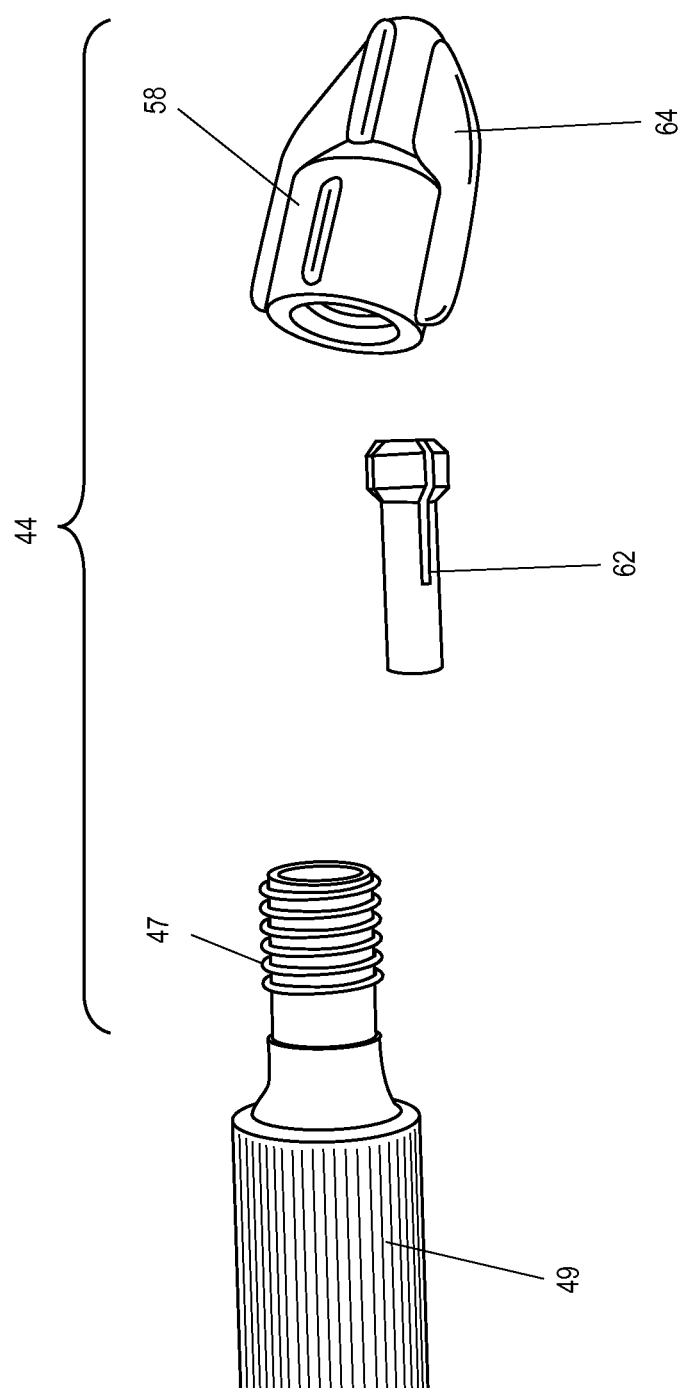
FIG. 9C shows a larger, exploded view of the locking mechanism of the handle of FIG. 9C.

As shown in FIGS. 9B and 9C, the handle includes several features that provide for safe, accurate, and controlled movement of the vascular device and/or the needle tipped guidewire through the vessels of a patient and through the desired exit location from the vessel. The handle 49 includes a reference portion 56, a slider 46, a groove 48 in which the slider moves from a proximal position (as shown in FIG. 9B) to a distal position (as shown in FIG. 9A), and a locking mechanism 44. For example, the handle, by way of the reference portion 56, facilitates accurately positioning the angled catheter tip 42, into a desired position within a vessel, as shown in FIG. 4. Furthermore, once the angled catheter tip 42 is positioned accurately within the vessel, the features of the handle (such as the slider 46, groove 48, and locking mechanism 44) facilitate the controlled, accurate movement of a needle tipped guidewire 50 through the catheter 40 and through the vessel, such that the needle tipped guidewire may exit the vessel in a safe and controlled manner, as shown in FIGS. 5 and 7D.

As shown in FIG. 9B, the handle includes a reference portion 56. As shown, the reference portion may be a tab or otherwise raised portion of the handle. Alternatively, the reference portion may be a surface feature such as an indent, a color, or any other suitable indicia. The position and/or orientation of the reference portion 56 with respect to the handle 49 indicates the position and/or orientation of the angled tip 42 with respect to the handle 49. For example, as shown in FIG. 9A, the reference portion may be on the same side of the handle as the angled tip of the catheter. As shown in FIG. 7D, once the catheter is inserted into the vessel, the handle 49 may be rotated such that the reference position 56 is moved to the desired position, thereby accurately moving the angled tip of the catheter to a desired position, such as pointing toward the exit site 25 of the vessel.

As shown in FIG. 9C, the handle includes a locking mechanism 44. The locking mechanism is coupled to the handle and is sized and configured to couple to a needle tipped guidewire. As shown, the locking mechanism may include a collet 62 that is placed within the proximal end of the handle 49 and a torque cap 58 which is placed over the collet 62 and coupled to the distal end of the handle 49 via screw grooves 47. The torque cap 58 may be threaded onto the handle, or coupled to the handle in any other suitable fashion. In some embodiments, the torque cap 58 includes wing(s) 64 that facilitate the tightening and loosening of the torque cap 58 and locking mechanism 44. As the torque cap 58 is tightened, it tightens the collet 62, which may then tighten around a needle tipped guidewire to secure the needle tipped guidewire within the handle. In alternative embodiments, the locking mechanism may alternatively include any other suitable locking mechanism such as a lever mechanism, cam mechanism, clamp mechanism, or any other suitable mechanism.

As shown in FIG. 4, as the catheter 40 and handle 49 are advanced over a general use guidewire 30, the locking mechanism may be loosened to allow the handle to slide over the guidewire. In some embodiments, the locking mechanism (or a portion thereof) may be removed from the handle to allow the handle to slide over the guidewire. Once the catheter and the handle are in place, as shown in FIG. 4, the guidewire may then be removed. Once the guidewire has been removed, the locking mechanism may be replaced back onto the handle and/or tightened onto the handle, such that the handle and locking mechanism may receive a needle tipped guidewire 50, as shown in FIG. 10A.

Figure 10A:
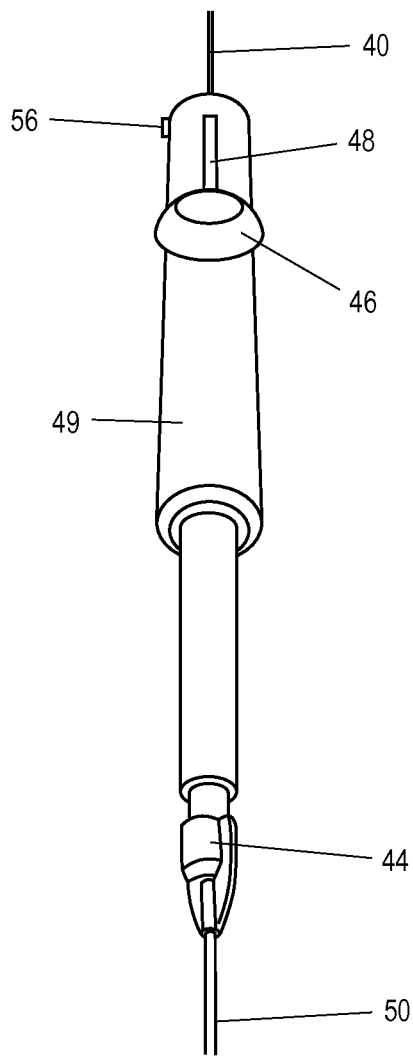
FIGS. 10A and 10B show an embodiment of a system having a needle tipped guidewire and a vascular device having an angled tip catheter and a handle having a slider, a reference portion, and a locking mechanism.

As shown in FIG. 10A, the handle 49 and locking mechanism 44 may receive a needle tipped guidewire 50. The needle tipped guidewire 50 may then be advanced through the handle 49 and the catheter 40 to a desired position. Once in the desired position, the locking mechanism 44 may secure the needle tipped guidewire 50 to a slider 46 disposed within the handle. As described in more detail below, and as shown in FIG. 10, the slider 46 is in in the proximal position within a groove 48 in the handle when the locking mechanism 44 is tightened around the needle tipped guidewire to provide the maximum advancement of the needle tipped guidewire 50 by the slider 46.

As shown in FIG. 5, the needle tipped guidewire 50 may be inserted into the handle 49 and catheter 40. The needle tipped guidewire may be advanced to a position, such as to the beginning (proximal end) of the angled tip. Once the needle tipped guidewire has been advanced, the locking mechanism 44 may be tightened to secure the needle tipped guidewire to the slider 46 within the handle 49. The needle tipped guidewire 50 may then be advanced from the catheter 40 through the desired exit site on the wall of the central blood vessel and skin of the patient, as shown in FIG. 5, by using the slider as described below. Prior to advancing the needle tipped guidewire from the catheter 40, the position of the angled tip 42 of the catheter may be verified by the position of the reference portion of the handle. Once the needle tipped guidewire 50 has exited the skin of the patient, the locking mechanism may be loosened such that the device may be removed from the patient while leaving the needle tipped guidewire in place.

As shown in FIGS. 9A and 9B, the handle includes a slider 48 and a groove 48 in which the slider moves from a proximal position (as shown in FIG. 9B) to a distal position (as shown in FIG. 9A). As shown, in FIG. 10B, the slider may be sized and configured to receive a thumb or other digit of a user's fingers and may be moved proximally and/or distally within the groove 48 by a user. The groove 48 may provide 5 to 10 cm of travel for the slider, for example, the groove may allow for 6 cm of travel of the slider within the handle.

Figure 10B:
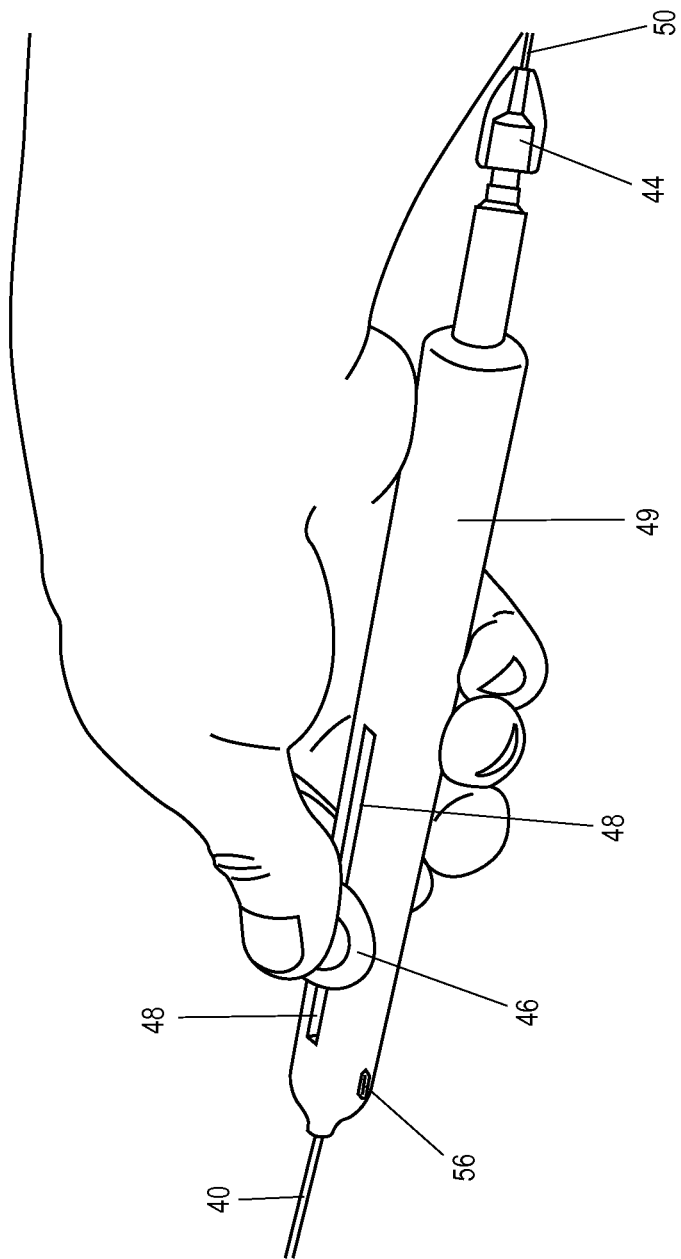

As described above, the needle tipped guidewire may be advanced to a desired position within the catheter, and the locking mechanism 44 may be tightened to secure the needle tipped guidewire to the slider 46 within the handle. The needle tipped guidewire 50 may then be advanced from the catheter 40 through the desired exit site on the wall of the central blood vessel and skin of the patient, as shown in FIG. 5, by using the slider. The slider functions to advance the needle tipped guidewire through the vessel and through the skin of a patient in a controlled manner. In one example, the needle tipped guidewire may be advanced manually or by any suitable means to a desired position within the catheter, such as to the proximal or beginning end of the angled tip. Once there, the locking mechanism may be tightened to secure the needle tipped guidewire within the catheter and to secure the slider mechanism to the needle tipped guidewire. As shown in FIG. 10A, the locking mechanism 44 is secured to the needle tipped guidewire 50 while the slider 46 is in the proximal position. Once the needle tipped guidewire is secured, the slider can be advanced to the distal position, as shown in FIG. 10B, thereby advancing the needle tipped guidewire 50 through the catheter 40. If the slider is advanced all the way to the distal position and the needle tipped guidewire has not been sufficiently advanced through the catheter, for example, the needle tipped guidewire has not yet penetrated the vessel and/or the skin of the patient, the locking mechanism may be loosened and the slider may be repositioned to the proximal position. Once the slider has been returned to the proximal position, the locking mechanism may be tightened again. Once the locking mechanism has been retightened, the slider may once again be advanced toward the distal position thereby advancing the needle tipped guidewire further through the catheter. These steps may be repeated until the needle tipped guidewire has been successfully advanced out of the catheter, through the vessel wall and out of the skin of the patient.

Figure 11:
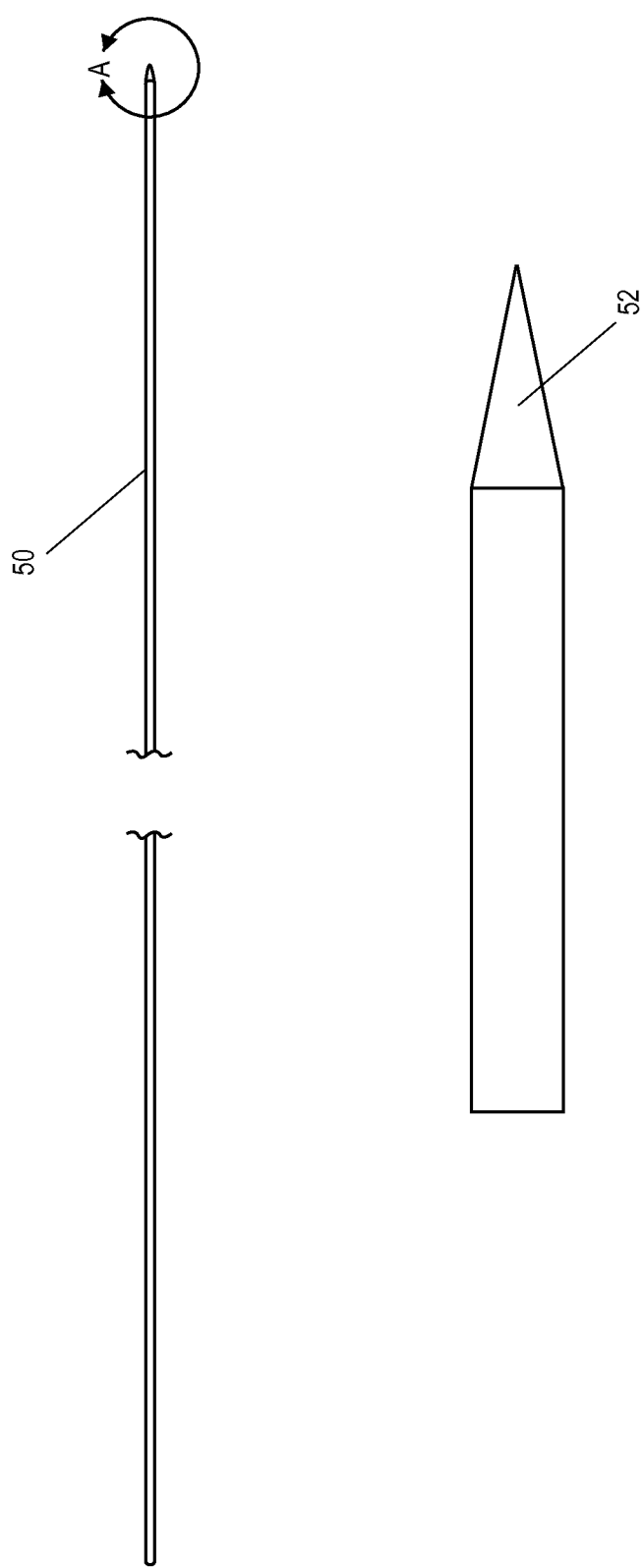
FIG. 11 shows an embodiment of a needle tipped guidewire that may be inserted into a vessel through the angled-tip vascular catheter and used to puncture the wall of a vessel.

A shown in FIGS. 11 and 10A-10B, a system for performing transvascular retrograde access placement in a vessel of a patient may include, in addition to a vascular device as described above, a needle tipped guidewire 50 comprising a sharpened tip 52, wherein the needle is sized and configured to pass through a desired exit site on the wall of the central blood vessel and skin of the patient. In some embodiments, the needle tipped guidewire may have an outer diameter of 0.035" or any other suitable diameter. The needle tipped guidewire 50 may be 180 to 220 cm in length. For example, the needle tipped guidewire may be 180 cm in length. Alternatively, the needle tipped guidewire may be any suitable length to be advance from a vessel insertion point to the exit point. For example, a needle tipped guidewire used in an antecubital vein, as shown in FIG. 8, may be shorter than a needle tipped guidewire sized and configured for insertion into a femoral vein, as shown in FIG. 5. As shown, the needle tipped guidewire 50 includes a sharpened tip 52 that facilitates passing the needle tipped guidewire through the desired exit site on the wall of the central blood vessel and skin of the patient. For example, the tip 52 may be a conical tip or any other suitable geometry with a penetrating tip.

The sharpened tip may be of any suitable length. For example, the tip 52 may have a length of 0.075" to 0.095", such as 0.085" or any other suitable length. In some embodiments, the needle tipped guidewire may have a surface finish such as a black oxide, or any other suitable finish to facilitate passing through a desired exit site on the wall of the central blood vessel and skin of the patient.

FIGS. 12A-12D show another embodiment of a transvascular retrograde access system according to this invention. The system 100 includes a catheter 102 and an actuation handle 104. A piercing wire 106 extends from a piercing wire push cap 108 through a luer lock 110 into and through handle 104 to the distal end of catheter 102. The distal tip 112 of piercing wire 106 is sharp, like a needle, as shown in FIG. 12D. An optional radiopaque marker band 114 may be disposed at or near the distal tip of catheter 102.

Actuation handle 102 may be used to bend the distal end of catheter 102. In the configuration shown in FIGS. 12A-D, the distal end of catheter 102 is unbent. A catheter tip deflection actuator 116 of handle 104 may be rotated about the handle's longitudinal axis to bend the distal end of catheter 102, such as to one or more preset angles, e.g., 45 degrees or 60 degrees. Handle 104 may be provided with indicators 117 showing the amount of tip deflection. Deflection of the catheter tip may be accomplished by using a steering wire running from the handle through the catheter, as is known in the art.

A collar 118 is attached to the piercing wire 106 within handle 104, and a spring 120 is disposed within the handle proximal to the collar. In the position shown in FIG. 12C, collar 118 holds spring 120 in a compressed configuration. A deployment button 122 extends into handle 104 to hold collar 118 and spring 120 in this configuration, and an optional safety slider 124 in the position shown in FIG. 12C acts as a safety interlock to prevent button 122 from being depressed inadvertently. Movement of slider 124 proximally permits button 122 to be depressed against the action of optional button springs 126 to an actuation position that permits spring 120 to expand and push collar 118 and piercing wire 106 distally. A detent 128 may be provided in handle 104 to interact with slider 124 as it moves proximally.

A second optional safety feature is an interlock that prevents actuation of the piercing wire unless the catheter tip has been deflected.

Unless defined otherwise, all technical terms used herein have the same meanings as commonly understood by one of ordinary skill in the art of vascular catheterization. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. Moreover, any one or more features of any embodiment of the invention can be combined with any one or more a features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A system for providing transvascular retrograde access in a central blood vessel of a patient, the system comprising:
   a handle;
   a catheter extending from the handle; and
   a tissue piercing element extending from the handle through the catheter, the tissue piercing element comprising a sharp distal tip adapted to extend from a distal portion of the catheter, a distal portion of the tissue piercing element being adapted to serve as a guide for introduction of a device into the central blood vessel,
   the handle including an actuator comprising a spring adapted to advance the tissue piercing element through an opening at the distal end of the catheter.

2. The system of claim 1 wherein a distal end of the catheter comprises an angled tip.

3. The system of claim 2 further comprising a reference at a proximal end of the catheter indicating a bending direction of the angled tip.

4. The system of claim 1 wherein the actuator further comprises a spring release element.

5. The system of claim 1 further comprising an interlock having a first state adapted to prevent actuation of the actuator and a second state adapted to permit actuation of the actuator.

6. The system of claim 1 further comprising a lock having a first state adapted to prevent movement of the tissue piercing element with respect to the actuator and a second state adapted to permit movement of the tissue piercing element with respect to the actuator.

7. The system of claim 1 wherein the handle comprises a deflection actuator adapted to deflect a distal tip of the catheter away from a longitudinal axis of the catheter.

8. The system of claim 1 wherein the handle further comprises a deflection indicator adapted to indicate an amount of deflection of the distal end of the catheter.

9. The system of claim 1 further comprising an interlock adapted to prevent movement of the sharp tip of the tissue piercing element out of the distal portion of the catheter unless the distal portion of the catheter is deflected away from a longitudinal axis of the catheter.

10. The system of claim 1 wherein the catheter and handle are adapted to be separated from the tissue piercing element.

* * * * *